(12) United States Patent
Carro Diaz

(10) Patent No.: US 11,422,137 B2
(45) Date of Patent: Aug. 23, 2022

(54) LACTOFERRIN FOR USE IN THE DIAGNOSIS OR PROGNOSIS OF ALZHEIMER'S DISEASE, OR IN THE DIAGNOSIS OF PARKINSON'S DISEASE

(71) Applicant: GEROA DIAGNOSTICS, S.L., Minano Mayor (ES)

(72) Inventor: Eva Maria Carro Diaz, Madrid (ES)

(73) Assignee: Geroa Diagnostics S.L., Minano Mayor (ES)

( * ) Notice: Subject to any disclaimer, the term of this patent is extended or adjusted under 35 U.S.C. 154(b) by 0 days.

(21) Appl. No.: 15/776,462

(22) PCT Filed: Nov. 17, 2016

(86) PCT No.: PCT/EP2016/078060
§ 371 (c)(1),
(2) Date: May 16, 2018

(87) PCT Pub. No.: WO2017/085214
PCT Pub. Date: May 26, 2017

(65) Prior Publication Data
US 2018/0328949 A1 Nov. 15, 2018

(30) Foreign Application Priority Data

Nov. 20, 2015 (EP) .................................. 15195662

(51) Int. Cl.
*G01N 33/68* (2006.01)
(52) U.S. Cl.
CPC ..... *G01N 33/6896* (2013.01); *G01N 2333/79* (2013.01); *G01N 2800/2821* (2013.01); *G01N 2800/2835* (2013.01)

(58) Field of Classification Search
CPC .......... G01N 33/6896; G01N 2333/79; G01N 2800/2821; G01N 2800/2835
See application file for complete search history.

(56) References Cited

FOREIGN PATENT DOCUMENTS

| WO | 02/39883 A2 | 5/2002 |
|---|---|---|
| WO | 2004037073 A2 | 5/2004 |
| WO | 2013014669 A1 | 1/2013 |
| WO | 2013153461 A2 | 10/2013 |

OTHER PUBLICATIONS

L. Wang, et al; Deposition of lactoferrin in fibrillar-type senile plaques in the brains of transgenic mouse models . . . ; Neuroscience Letters; 481; 2010; pp. 164-167.
R. Talebi, et al; Parkinson's disease and lactoferrin: Analysis of dependent protein networks; Gene Reports; 4; 2016; pp. 177-183.
International Search Report and Written Opinion dated Mar. 31, 2017 for PCT/EP2016/078060.

*Primary Examiner* — Olga N Chernyshev
(74) *Attorney, Agent, or Firm* — Wolf, Greenfield & Sacks, P.C.

(57) ABSTRACT

The present invention is the protein of lactoferrin, or an encoding nucleic acid of same, for use in the diagnosis or prognosis of Alzheimer's disease (AD). The invention is a method of diagnosis or prognosis of AD in a subject, comprising assessing the level of lactoferrin in the saliva or in a saliva sample of said subject and determining whether said level is above or below a value of 7.43 μg/ml, wherein a value below 7.43 μg/ml is indicative of AD or of the prognosis of AD. Another aspect is the protein of lactoferrin, or an encoding nucleic acid of same, for use in the diagnosis of Parkinson's disease (PD) in a saliva sample of a subject.

5 Claims, 6 Drawing Sheets
Specification includes a Sequence Listing.

LACTOFERRIN FOR USE IN THE DIAGNOSIS OR PROGNOSIS OF ALZHEIMER'S DISEASE, OR IN THE DIAGNOSIS OF PARKINSON'S DISEASE

CROSS REFERENCE TO RELATED APPLICATION

This Application is a 371 of PCT/EP2016/078060 filed on Nov. 17, 2016, which claims priority of European Application No. 15195662.0 filed Nov. 20, 2015, both of which are incorporated herein by reference.

FIELD OF THE INVENTION

The present invention is of application in the medical science, in particular in the diagnosis of the Alzheimer's disease and Parkinson's disease.

BACKGROUND OF THE INVENTION

Alzheimer's disease (AD) accounts for the most cases of dementia. The disease takes decades to develop entirely, sharing many pre-symptomatic effects with other degenerative dementias whose first clinical show up as Mild Cognitive Impairment (MCI). The first symptoms of AD are often mistakenly attributed to ageing or stress.

AD is currently diagnosed based on the person's medical history, history from relatives and behavioural observations. Detailed neuropsychological testing can reveal mild cognitive difficulties several years before a person fulfils the clinical criteria for diagnosis of AD. Subtle problems with the executive functions of attentiveness, planning, flexibility, and abstract thinking or impairments in semantic memory can also be symptomatic. Assessment of intellectual functioning including memory testing can further determine the state of the disease.

All attempts by practising physicians to create diagnostic criteria that may enable to facilitate and standardise the diagnostic process follow these parameters. At present, a definitive AD diagnosis requires the histopathological confirmation including microscopic examination of brain tissue.

The current definition or diagnosis of AD is clinical. The clinical diagnosis is, in most cases, absent of biological markers. Only monogenetic cases of familiar AD own genetic markers, and these count for less than 2% of all cases of the disease. The discovery by Kane that the ApoE4 allele is a risk factor for Alzheimer's-type dementia for increasing the risk and influencing age of onset has had more scientific than clinical importance, and shows little diagnostic power (Kane R A, Kane R L. "Effect of genetic testing for risk of Alzheimer's disease". N. Engl. J. Med. 2009, 361(3), 298-299).

The strongest biomarker candidates for AD include brain-imaging studies at magnetic resonance imaging or positron emission tomography, and proteins such as beta-amyloid and tau in cerebrospinal fluid (CSF). Emphasis in AD research has been placed on diagnosing the condition before symptoms begin. A number of biomarkers and biochemical tests have been used and developed to allow for AD early detection.

Some of the great drawbacks of using protein-based tests include the elevated costs, the need of invasive procedures and the complications arising from the interpretation of results, which make them unable for an extended use. For example, neuroimaging of cortical amyloid burden and volumetric changes in the brain and assessment of protein concentrations in CSF are diagnostic tools that are not widely available.

Proteins of autolysosomes in blood levels are also capable of differences between controls and ill population between 1 and 10 years before being diagnosed (Goetz) et al., "Altered lysosomal proteins in neural-derived plasma exosomes in preclinical Alzheimer's disease", Neurology 2015, Jul. 7; 85(1):40-7). Another recent study has validated some previously described plasma biomarkers capable to predict conversion to dementia from prodomic stages (Hye et al., "Plasma proteins predict conversion to dementia from prodromal disease". Alzheimer's & Dementia 2014, 10, 799-807). However, all these studies have focused on a set or panel of biomarkers, including proteins, lipids or other metabolites. In general, biomarkers are comprised among beta-amyloid and tau derived molecules. These potential biomarkers render as indicators of an already started disease, withdrawing the possibility of a real early detection or prognosis. In this sense, the present invention corresponds well with the scientific consensus in the need for a diagnosis at the stadium pre-dementia of AD.

Several works have been recently published describing detectable molecular or biochemical alterations before the appearance of early symptoms of dementia, such as the reduction in plasma levels of phospholipids (Mapstone et al, "Plasma phospholipids identify antecedent memory impairment in older adults". Nat. Med. 2014, 20 (4) 415-420). This study was able to predict MCI or AD within 2-3 year timeframe using a panel of ten lipids from peripheral blood. The limitation of time is significant.

The recent attempt by Dubois to establish a diagnosis of AD pre-dementia based on strict clinical criteria, neuroimaging tests and biological data mainly in CSF is of interest looking for a better defined clinical phenotypes in order to integrate biomarkers into the diagnostic process, to get to disease-modifying or preventive therapies (Dubois et al. "Advancing research diagnostic criteria for Alzheimer's disease" Lancet Neurol. 2014 June; 13(6):614-29). However, current biomarkers render unsatisfactory because they are either invasive, time-consuming or expensive, including the determination level in CSF or structural and functional magnetic resonance imaging.

The application US 20140602046 A1 describes the treatment of AD comprising the administration of a specific antibody against peptides derived from the tau protein. The document refers to the slow progression of the disease and to the prevention by an asymptomatic subject. Prophylactic administration is recommended to the whole population over 10 years old. As mentioned above, the tau isomers to be detected are very probable produced in the body once the disease has developed, discarding the prognosis.

US 20110236917 A1 describes a method of diagnostic of AD in a subject comprising the detection of a panel of forty-seven (47) biomarker proteins in a serum sample of a subject. Transferrin I and II are disclosed among the markers of the panel. A first drawback of these teachings is the need of a serum sample, for which extraction it is required a professional practitioner. Besides, no protein of the set is particularly suggested among the others for contributing with more accurate information. Based in the teachings of this document, the expert would have not found suggested to search for any protein relevant by itself for the diagnose of AD in a subject. Indeed, the ideal single biomarker enabling prediction or early detection of AD has not yet been identified.

Several research lines have indicated a possible correlation between the inflammation of the brain and oral health. Recently, the number of publications related to salivary proteomic has increased significantly proposing human saliva as a biological fluid for diagnostics. Saliva has many advantages in terms of low invasiveness, minimum cost and easy collection and processing. Presence of proteins A and tau in human saliva has been described, suggesting their usefulness as potential biomarker for AD (Shi et al., "Salivary tau species are potential biomarkers of Alzheimer's disease". J Alzheimer's Dis. 2011; 27(2):299-305). Other proteins have been described in salivary samples, including those associated with inflammatory responses and pathogenesis of AD (Ciregia et al., "A multidisciplinary approach to study a couple of monozygotic twins discordant for the chronic fatigue syndrome: a focus on potential salivary biomarkers." J Transl Med. 2013 Oct. 2; 11:243).

At this respect, WO 2013/153461 A2 describes the diagnosis of the AD after two biomarkers chosen out of a set of molecules present in saliva. Again, the referred proteins are rather indicative of an already started disease, and therefore the obtained results cannot be used for prognosis of the disease.

Lactoferrin is an iron-binding glycoprotein of the family of the transferrins, which has been extensively used in the diagnostic of inflammatory diseases. The molecule suppresses the production of inflammatory cytokines and modulates oxidative stress. It is also associated with protection of brain tissue from oxidative damage in other neurodegenerative diseases, including Parkinson's disease (PD), and has been detected in tau protein neurofibrillary tangles and amyloid beta (Aβ) senile plaques, which are the main histopathological hallmarks in AD along neuronal death (Wang et al., "Deposition of lactoferrin in fibrillar-type senile plaques in the brains of transgenic mouse models of Alzheimer's disease". Neurosci Lett 2010; 481: 164-7). The protein is one component of human secretions synthesized by exocrine glands and neutrophils in infection/inflammation sites. Among salivary proteins, it is the most important factor of natural immunity, representing in saliva an important defense factor against bacterial injuries.

Welling discloses some Anti-Microbial Peptides (AMPs) permeable to the Blood-Brain Barrier (BBB) (Welling m. et al. "Potential role of antimicrobial peptides in the early onset of Alzheimer's disease", Alzheimer & Dementia, 11, p.51-57, 2015). The publication highlights the ability of lactoferrin to cross the BBB when administrated to the patient, or turning upregulated during infectious processes. Besides, it proposes the possible use of AMPs in the detection of brain infections in vivo. However, any relation that could be established between the notice of its up regulation at infectious process and an effective use in the diagnose of AD renders speculative.

Lactoferrin has been taught by US 2003/0096736 A1, however, to be useful in the treatment of several diseases including neurodegenerative diseases, and in particular AD. No relation is made or hint given towards the molecule being used in the diagnosis or prediction of any other neurodegenerative disease, in particular of AD.

The art has not disclosed lactoferrin for use in the diagnosis and/or prognosis of AD.

WO 2009074331 A3 is considered the closest prior art to the present invention. The aim of this document is to describe an AD early-diagnose method comprising the detection of a protein product of several genes in a biological sample of a subject. The products of the transferrin (TF) gene are comprised in these biomarkers, as well as those of else other genes as IGF-1R or HISTIH3E. The proposed genes do not have any relationship among them after any biological ground, all showing similar predictive values to be used in the method. In particular, there is no TF-gene product suggested for use among any other, as well as not lactoferrin. The resulting scope of the application in terms of gene products is unfeasible, and renders as an undue amount of work for an expert to test for the diagnosis of the disease. Yet it is specified that the biological sample comprises saliva, the examples are performed in blood samples. The document identifies the major problem of the diagnostic methods of the art only being able to detect the disease in a patient already suffering of same, thereby not to establish a prognosis and a possible preventive action. However and despite the expectations of the authors, it must be said that the problem remains unsolved. On the tested populations of patients, the tested genes HIST3H3E and CNR2 reveal capable to show the presence of the disease indeed, in no case however are useful for the prognosis. In addition, none of them are related to lactoferrin.

The problem of the art is still formulated as the finding of a single biomarker for the diagnostic or prognosis of Alzheimer's disease. The solution proposed by the present invention is a method detecting the level of lactoferrin in a subject.

With respect to PD, the neuronal upregulation of lactoferrin in the brain of the patients is known in the art (Faucheux, B. A., et al. "Expression of lactoferrin receptors is increased in the mesencephalon of patients with Parkinson disease." *Proc Natl Acad Sci USA* 92, 9603-9607, 1995; Leveugle, B., et al. "Cellular distribution of the iron-binding protein lactotransferrin in the mesencephalon of Parkinson's disease cases". *Acta Neuropathol* 91, 566-5726, 1996). However and to the extent of the knowledge of the inventors, the art does not teach or suggest about the regulation of the protein in saliva. In beforehand, no direct link can be made on the metabolite presence in each biological fluid.

The problem with respect to PD can be set on the finding of a single biomarker for the diagnosis of the disease. The solution proposed by the present invention is a method detecting the level of lactoferrin in saliva.

DESCRIPTION OF THE INVENTION

The present invention is lactoferrin, or a nucleic acid molecule encoding same, for use in the diagnosis or prognosis of AD. In a preferred aspect, said diagnosis or prognosis is performed in a biological sample of a subject selected from mucous tissue, preferably oral mucous tissue, and saliva. Alternatively, the invention is the use of lactoferrin in the diagnosis or prognosis of AD in the saliva or in a saliva sample of a subject.

In the scope of the present invention, the term "diagnosis" includes a certain grade of evolution of the disease that can be measured in the patients, whether the statement is AD or the first symptoms of MCI in any of its stages.

In the scope of the present invention, the term "prognosis" is understood as the prediction of AD when no phenoconversion into symptoms are yet detectable in a healthy subject.

Protein cut-off values were derived for lactoferrin protein identified in the diagnostic training study. The predictive value of phenoconversion to MCI/AD was <7.43 µg/ml. This means, that all subjects with MCI or AD diagnosis exhibited saliva lactoferrin values lower than 7.43 µg/ml, and all healthy control subjects exhibited saliva lactoferrin values higher than 7.43 µg/ml.

Based on this, another aspect of the invention is a method of diagnosis of AD in a subject, comprising assessing the level of lactoferrin in the saliva or in a saliva sample of said subject, and determining whether said level is above or below a value of 7.43 µg/ml, wherein a value below 7.43 µg/ml is indicative of AD. If the level of lactoferrin is below 7.43 µg/ml and the subject shows phenoconversion of a neurological disease, then the method is indicative of AD.

Still another preferred aspect of the invention is a method of prognosis of AD in a subject, comprising assessing the level of lactoferrin in the saliva or in a saliva sample of said subject, and determining whether said level is above or below a value of 7.43 µg/ml, wherein a value below 7.43 µg/ml is indicative of the prognosis of AD. If the level of lactoferrin is below 7.43 µg/ml and the subject does not show phenoconversion of a neurological disease, then the method is indicative of the prognosis of AD.

The present application shows lower levels of lactoferrin in human saliva from MCI and AD patients compared with age-matched control, suggesting that this protein may be involved in early stages of AD. It is postulated that measures of reduced saliva levels of lactoferrin is specific of AD pathology.

In the scope of the present invention, the determination of the presence of lactoferrin in saliva does not include any invasive or surgical step that could involve substantial risk for the health of the subject, irrespective of whether said determination is performed ex-vivo or in-vivo.

The present application shows that saliva lactoferrin levels are able to unequivocally distinguish cognitively normal subjects who will progress to either MCI or AD within 5 years from those destined to remain cognitively normal in the future. To our knowledge, this is the first single biomarker described capable to predict phenoconversion within 5-year timeframe with 100% accuracy. The present invention is even able to predict phenoconversion MCI and/or AD from healthy status within a 9-year timeframe.

Logistical regression analysis using a combination of saliva lactoferrin levels and age at the time of saliva sample collecting accurately classified the subjects as either young or aged-groups (FIG. 5A), and within aged-groups, phenoconverters to MCI/AD and non-phenoconverters (FIG. 5B).

The phenoconversion time was determined through an analysis of linear regression, using the correlation between depletion of lactoferrin levels in saliva with the phenoconversion onset. Lower lactoferrin levels were associated with increased risk of phenoconversion of AD in this model (FIG. 6). Saliva lactoferrin levels came up to be related to changes in the time of onset of phenoconversion.

At this respect, the regression analysis generated the equation $$y=0.6289x+1.6954$$

that describes the relationship between saliva lactoferrin levels and the time in years of onset. In this formula, "y" is the saliva lactoferrin levels and "x" the time in years of phenoconversion. Applying this equation in a hypothetic case of a subject with saliva lactoferrin levels lower than the cut-off value, for example to 7.43 µg/ml, the resulting timeframe is of more than 9 years of phenoconversion to MCI/AD.

Therefore, in another preferred aspect, said prognosis is up to a timeframe of nine years before the subject shows phenoconversion of AD, more preferably up to eight years, seven years, six years or five years.

In another preferred aspect of the invention the subject is a mammal, more preferably human.

As per in saliva, similar results obtained from tears and oral mucosa pellets indicate that lactoferrin levels from peripheral non-invasive body samples might be used as diagnostic tool for AD. It is possible that saliva lactoferrin represents a first defence line even before brain pathological and/or clinical alterations were detected, and its reduction in MCI subjects may be consider as an early AD biomarker.

Indeed, a similar decrease of the level of lactoferrin in saliva was also detectable in oral mucosa obtained from a pilot study using two groups, healthy control and AD groups paired in age and sex. The levels of lactoferrin in AD patients were significantly reduced compared to healthy control subjects, which is 4.35±0.88 µg/ml in AD vs 10.78±1.9 µg/ml. Data expressed as mean±standard deviation (SD).

The model used in the present invention classified diseased groups (MCI/AD) and healthy control subjects with an AUC of 1 with 95% confidence interval (CI) (1-1), for the MCI/AD vs healthy control classification (FIG. 4B). These data are however not reproducible either in blood samples or CSF.

Based in these results, it renders suggested to consider any iron binding glyco-protein of the transferrin family being a potential marker of AD.

Another preferred aspect is a kit for performing the method of the present invention, comprising at least one reagent for the quantification of lactoferrin in the saliva or in a saliva sample of a subject, and enabling the comparison of said quantification with a predetermined cut-off value, preferably 7.43 µg/ml. In a more preferred aspect, said reagent is an antibody specific for lactoferrin.

In the scope of the present invention, an antibody specific for lactoferrin is meant to be an antibody capable of specifically recognising lactoferrin.

Yet another preferred aspect, is a kit including at least one container that contains specific pharmaceutical formulations for the quantification of lactoferrin in the saliva or in a saliva sample of a subject, instructions for the use of said formulations and a dispositive for determining whether the result of the quantification of lactoferrin are above or below a predetermined cut-off value indicative of AD or of the risk of developing AD in said subject, preferably 7.43 µg/ml.

The invention offers the possibility of managing the diagnosis or the prognosis of a wide number of patients in else centres than those wherein the biological samples are obtained. In this sense, a further aspect of the invention is a system for the prediction of the evolution of a subject to AD comprising data processing means, said data processing means been configured to assess in saliva sample the level of lactoferrin or of a nucleic acid molecule encoding same, to determine whether said level of lactoferrin is below a predetermined cut-off value, preferably 7.43 µg/ml, and to predict the functional outcome of AD in the subject evaluating the result of the previous determination.

On the contrary, the lactoferrin levels in saliva of Parkinson's disease (PD) patients showed significantly higher levels to those observed in the control healthy group (FIG. 2B). Pair-wise comparisons between PD and control healthy groups showed significant alterations, 12.61±3.31 µg/ml in PD vs 10.78±1.0 µg/ml in healthy control group. Data expressed as mean±SD. These findings are in agreement with neuronal upregulation of lactoferrin in PD patients, as previously reported.

The measure of lactoferrin also found a correspondence in PD patients. Indeed, another aspect of the present invention refers to lactoferrin, or a nucleic acid molecule encoding same, for use in the diagnosis of Parkinson's disease in the saliva or in a saliva sample of a subject. In a preferred aspect, said subject is a mammal, more preferably human.

EXAMPLES

Figure 1A:
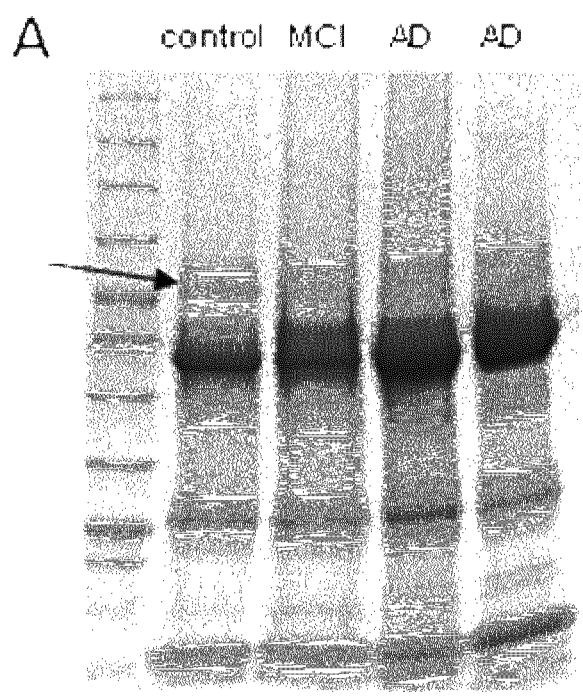
FIG. 1A shows a 75 kDa lactoferrin band after SDS-PAGE fractionation present in all samples. Identification of lactoferrin in human saliva from MCI, AD, and healthy controls. Coomassie blue staining PAGE-SDS gel corresponding to saliva pools. Lane 1, control group; lane 2, MCI group; lane 3, and 4 AD group. Band corresponding to around 75 kDa is signed with arrow.

The following examples are provided for the purpose of showing the present invention in an illustrative yet non-limiting manner.

Example 1. Extraction of Saliva Samples

An AD diagnostic training study was carried out enrolling 274 participants at the Neurology Service at the Hospital Universitario 12 de Octubre (Madrid, Spain). Four (4) groups of age-matched subjects according to their cognitive status were defined: aMCI, AD, Parkinson's disease (PD) and cognitively healthy control group (Table 1). For AD patients, diagnosis was established according to the National Institute on Neurological Disorders and Stroke, and the Alzheimer's Disease and Related Disorders Association (NINDS-ADRDA) guidelines (McKhann et al., "The diagnosis of dementia due to Alzheimer's disease: recommendations from the National Institute on Aging-Alzheimer's Association workgroups on diagnostic guidelines for Alzheimer's disease". Alzheimer's Dement. 2011; 7: 263-9). PD patients were diagnosed under the criteria of probable PD (Gelb et al., "Diagnostic criteria for Parkinson disease". Arch Neurol. 1999 January; 56(1):33-9). A group of MCI patients were also added defined after patients with cognitive impairment that did not fulfill the criteria for dementia (Pedersen, "Mild cognitive impairment as a diagnostic entity". J Intern Med 2004; 256: 183-94). Disease severity was evaluated using Mini-Mental State Examination (MMSE) scores. Subjects' consent was obtained according to the Declaration of Helsinki, and approval was obtained from the Research Ethic Committee of Hospital 12 de Octubre. Unstimulated whole saliva was collected into sterile plastic containers pre-coated with 2% sodium azide solution, as previously described by Bermejo-Pareja (Bermejo-Pareja et al., "Saliva levels of Abeta1-42 as potential biomarker of Alzheimer's disease: a pilot study". BMC Neurol 2010; 10: 108). Collected samples were immediately placed on ice and pre-cleared by a low spin at 600×g for 10 min at 4° C. Aliquoted 0.5 ml samples were stored at −80° C. after treatment with Protease Inhibitor Cocktail (Roche). Protein estimation was analyzed using a BCA protein assay kit (Pierce, Rockford, Ill.) according to the manufacturer's instructions.

TABLE 1

Demographic, and clinical characteristics of subjects from first training study.

| Variable | Control | aMCI | AD | PD | p value |
|---|---|---|---|---|---|
| n (F/M) | 91 (59/32) | 44 (25/19) | 80 (49/31) | 59 (32/27) | ns |
| Age (years) | 73.7 ± 6.88 | 75.16 ± 5.13 | 76.2 ± 5.33** | 69.5 ± 8.6** | p < 0.01 |
| MMSE score | 29 ± 0.8 | 26.8 ± 1.16*** | 19.25 ± 1.76*** | NA | p < 0.001 |
| APOE ε4 carriers | 12.9% | 42.1%** | 45.9%** | NA | p < 0.01 |

M = male; F = female; aMCI = amnestic Mild Cognitive Impairment; AD = Alzheimer's disease; PD = Parkinson's disease; MMSE = mini-mental state examination scores; NA = not applicable; ns = not significant.
Data are expressed as mean ± S.D.
**p < 0.01 versus control group;
***p < 0.001 versus control group.

Example 2: Measure of Lactoferrin in the Saliva Samples

Human lactoferrin according to SEQ.ID.NO.:1 expression levels in saliva were detected in pooled samples from 5 AD patients compared to MCI donors and control subjects. Saliva samples from 4 male subjects from each group (MCI, AD, and elderly non-demented controls) were pooled by mixing equal amounts. 50 µg of each pool were loaded on a SDS-PAGE gel. After SDS-PAGE fractionation a 75 kDa band was detected in all samples matching with the lactoferrin molecular weight as confirmed by mass spectrometry analysis (31% coverage). Differences in protein expression were evaluated in using ImageQuant software (GE Healthcare). Upon equal amount of protein loaded, the band intensity analysis showed reduced lactoferrin levels in MCI (14%) and AD (51% and 58%) compared to the healthy control group (FIG. 1A). To validate the presence of lactoferrin in human saliva, this protein was identified by MALDI-TOF/TOF mass spectrometer 4800 Proteomics Analyzer (Applied Biosystems, Framingham, Mass.) and 4000 Series Explorer™ software (Applied Biosystems) after in gel digestion with trypsin and endopeptidase Asp-N (Thermo Fisher Scientific). The amino acid coverage was 31% for lactoferrin.

Figure 2A:
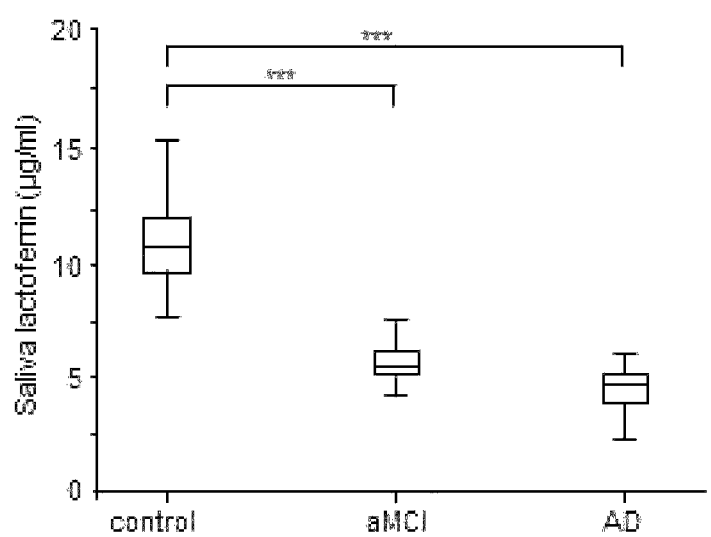
FIG. 2A shows that saliva levels of lactoferrin, measured by human ELISA kit, were decreased in MCI and AD patients compared with control group.
Figure 2B:
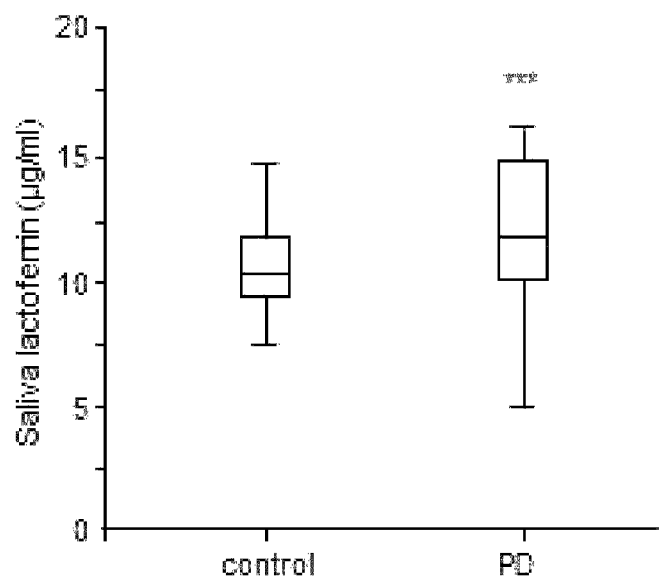
FIG. 2B shows that saliva levels of lactoferrin, measured by human ELISA kit, were increased in PD compared with control group.

Further confirmation of these differences was obtained averaging the lactoferrin expression levels by a commercial lactoferrin human ELISA kit (Abcam), according to the manufacturer's instructions. Pair-wise comparisons between the three groups, using ANOVA followed by a Tuckey-Kramer test, showed a significant reduction in lactoferrin levels in MCI and AD patient groups relative to healthy control group ($p<0.05$; FIG. 2A). Lactoferrin levels in PD saliva showed significantly higher levels to those observed in the control healthy group (FIG. 2B).

Example 3. Saliva Lactoferrin Content as Diagnostic Tool

Figure 3A:
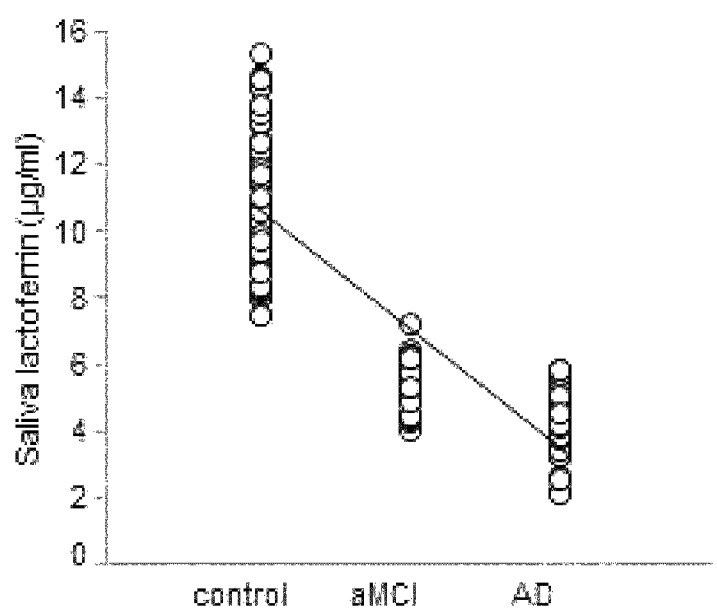
FIG. 3A shows a correlation between saliva levels of lactoferrin and cognitive decline in MCI and AD groups. This relation was driven primarily by a significant negative association between stages of disease and lactoferrin levels ($R=-0.74$; $p<0.001$).
Figure 3B:
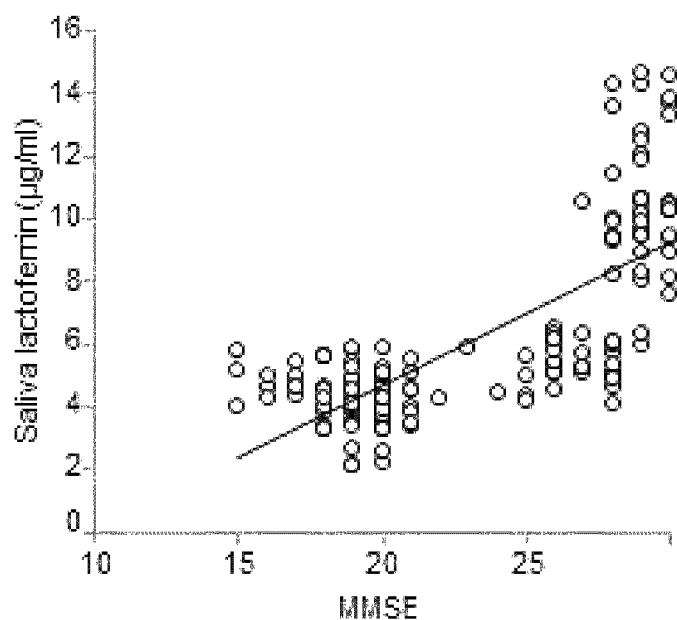
FIG. 3B shows a correlation between saliva levels of lactoferrin and MMSE score, a measure of cognition available in patients with MCI and AD ($R=0.73$; $p<0.001$).

Saliva levels of lactoferrin were evaluated throughout the progression of dementia. Correlation between saliva lactoferrin levels and cognitive decline in MCI and AD groups seems evident. This relation was driven primarily by a significant negative association between stages of disease and lactoferrin levels ($R=-0.742$; $p<0.001$) (FIG. 3A). The MMSE score was used to following up the progression of dementia. The saliva lactoferrin concentration could also be correlated with MMSE score in patients with MCI and AD, after a highly significant correlation ($R=0.731$; $p<0.001$) (FIG. 3B) to 15 and 10 µg/ml in healthy humans, and less than 7.43 µg/ml in demented humans, including MCI and AD. The Kendall's tau and Spearman rank correlation were used for correlation analyses, respectively.

Figure 3C:
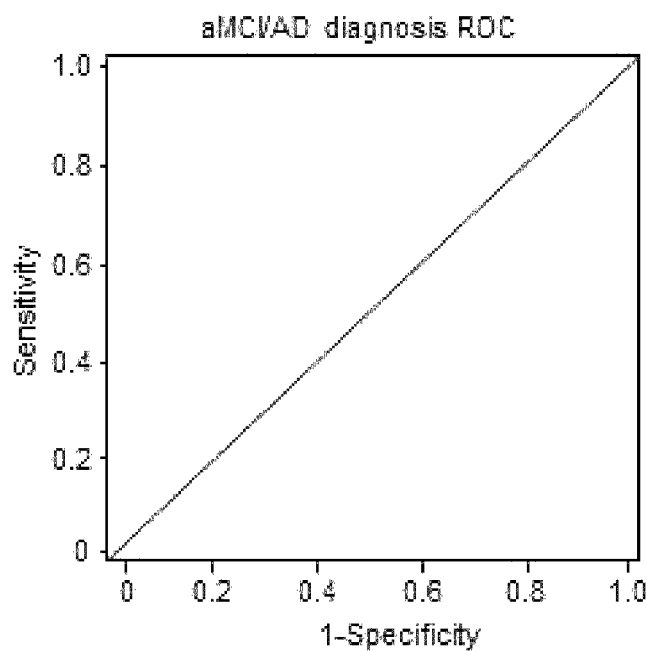
FIG. 3C shows the ROC curve obtained for the test of saliva lactoferrin levels from the full control group and MCI/AD group. The ROC plot represents sensitivity (true positive rate) versus 1-specificity (false positive rate). The area under the ROC curve AUC=1 (95% CI 1-1).

Using linear regression analysis, we discovered that patients suffering from AD and aMCI had 6.432 µg (95% CI: 6.850-6.014; $p<0.001$) and 5.310 µg (95% CI: 5.810-4.810; $p<0.001$) of salivary lactoferrin per ml less than cognitively healthy participants respectively. We used these results from the lactoferrin analysis to build separate linear classifier models that would distinguish the aMCI/AD groups from the control group, and we did receiver operating characteristic (ROC) analysis to assess the performance of the classifier models for group classification. A classifier model using the discovered lactoferrin levels from saliva analysis yielded an area under the curve (AUC) of 1 (95% CI 1-1), being the sensitivity 100% (95% CI 96.90%-100%) and specificity 100% (95% CI 95.95%-100%) for aMCI/AD and healthy control group classification (FIG. 3C). The cut-off value was 7.43 µg/ml (Youden index: 1).

Example 4. Validation of Saliva Lactoferrin as Diagnostic Tool

The cut-off value of saliva lactoferrin was then validated in two new blinded and independent cohorts enrolling 91 additional participants with the same standardized clinical assessments used in the previous study. Demographic characteristics of participants recruited in two entities: Alzheimer Disease Research Unit, CIEN Foundation, Queen Sofia Foundation Alzheimer Center (Madrid, Spain), and Pablo de Olavide University from Sevilla, Spain, are shown in Table 2.

TABLE 2

Demographic, characteristics of subjects from validation study.

| Variable | Control | aMCI | AD | p value |
|---|---|---|---|---|
| n (F/M) | 40 (25/15) | 15 (5/10) | 36 (23/13) | ns |
| Age (years) | 66.78 ± 7.33 | 68.93 ± 6.12 | 80.67 ± 8.76*** | $p < 0.001$ |

F = female; M = male; aMCI = amnestic Mild Cognitive Impairment; AD = Alzheimer's disease; ns = not significant.
Data are expressed as mean ± S.D.
***$p < 0.001$ versus control group.

Results showed that cut-off value of saliva lactoferrin (7.43 µg/ml) classified correctly all patients (MCI/AD; n=51) and all cognitively healthy subjects (n=40).

Example 5. Saliva Lactoferrin Content as Predictive Tool

In order to investigate predictive potential of lactoferrin levels in saliva, cognitively healthy control participants, without memory impairment, integrated this group (Table 3).

TABLE 3

Demographic characteristics of subjects.

| Subjects | No. | M/F | Age (mean ± SEM) |
|---|---|---|---|
| Controls (non demented) | 116 | 45/71 | 68.06 ± 1.12 |

M = male, F = female.

Unstimulated whole saliva was collected into sterile plastic containers, and lactoferrin levels were determined as described in Example 1. Eight (8) subjects showed significantly reduced levels of lactoferrin in saliva compared to a healthy control group (3.47±0.41 µg/ml vs 10.54±1.58 µg/ml; $p<0.05$). The average time for phenoconversion to either MCI or AD was 3.25 years (range 1-5 years). Table 4 shows the presence of an association between time of phenoconversion (onset) and age, being shorter with older subjects.

TABLE 4

Demographic characteristics of converters.

| Subjects | Sex | Age | onset | Lt levels (µg/ml) | Neurological diagnose | Other clinical diagnose |
|---|---|---|---|---|---|---|
| 1 | M | 82 | 2 | 3.01 | MCI | HT, DM |
| 2 | F | 70 | 4 | 3.17 | MCI | |

TABLE 4-continued

Demographic characteristics of converters.

| Subjects | Sex | Age | onset | Lt levels (µg/ml) | Neurological diagnose | Other clinical diagnose |
|---|---|---|---|---|---|---|
| 3 | F | 71 | 5 | 3.69 | MCI | HT, HC |
| 4 | F | 68 | 5 | 5.10 | MCI/AD | |
| 5 | F | 81 | 1 | 1.65 | MCI/AD | |
| 6 | F | 77 | 2 | 1.89 | MCI | HT |
| 7 | M | 83 | 3 | 6.18 | MCI/AD | HT, DM, HD |
| 8 | M | 88 | 4 | 4.45 | MCI | HT |

Lt = lactoferrin;
AD = Alzheimer's disease;
MCI = Mild Cognitive Impairment;
M = male,
F = female;
HD = Hypertension,
DM = Diabetes Mellitus;
HD = Heard Disease;
HC = Hypercholesterol.

Example 6. Mucosa Lactoferrin Contents

Oral mucosa was collected into sterile plastic containers according to Aagaard (Aagaard et al., "The Human Microbiome Project strategy for comprehensive sampling of the human microbiome and why it matters". FASEB J. 2013 March; 27(3):1012-22). Briefly, participants, described in Table 5, drooled into a 50-ml collection tube after allowing saliva to collect in the mouth for minute, centrifuged at 6000×g for 10 min at 4° C., and pellets were stored at −80° C.

TABLE 5

Demographic characteristics of subjects.

| Subjects | No. | M/F | Age (mean ± SEM) |
|---|---|---|---|
| Controls (non demented) | 190 | 110/80 | 62 ± 1.23 |

M = male, F = female.

(Lactoferrin levels were determined as described in Example 1. Six (6) subjects showed significantly reduced levels of lactoferrin compared to a healthy control group (4.28±0.50 µg/ml in AD vs. 9.05±1.47 µg/ml; p<0.05; Table 6). The average time for phenoconversion to either MCI or AD was 3.83 years (range 4-3 years). Cognitively healthy control participants, without memory impairment, integrated the group shown in Table 5.

TABLE 6

Demographic characteristics of converters.

| Subjects | Sex | Age | onset | Lt levels (µg/ml) | Neurological diagnose |
|---|---|---|---|---|---|
| 1 | F | 96 | 4 | 5.02 | AD |
| 2 | M | 66 | 4 | 3.66 | MCI |
| 3 | M | 82 | 4 | 2.51 | AD |
| 4 | M | 67 | 4 | 5.92 | MCI |
| 5 | M | 84 | 4 | 4.17 | AD |
| 6 | M | 85 | 3 | 4.13 | MCI/AD |

Lt = lactoferrin; AD = Alzheimer's disease; MCI = Mild Cognitive Impairment; M = male, F = female.

Example 7. Build of a Predictor Model of Phenoconversion to MCI/AD

Figure 4A:
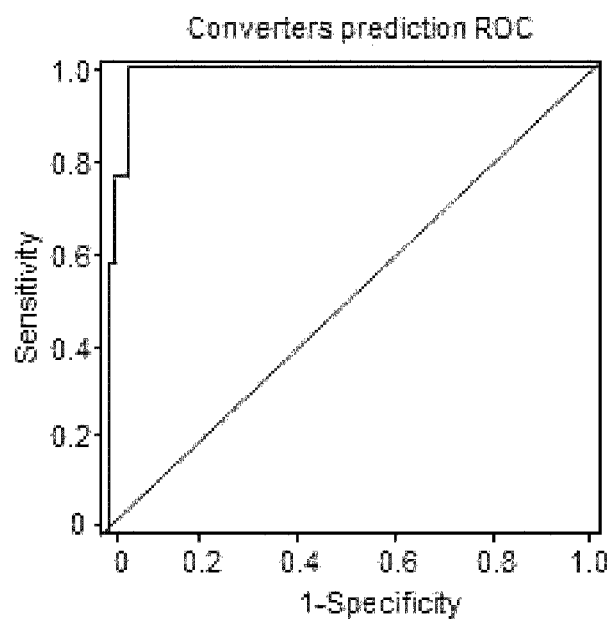
FIG. 4A shows the receiver operating characteristic (ROC) curve obtained for the test of saliva lactoferrin levels from the full control group and converter group. The ROC plot represents sensitivity (or true positive rate) versus 1-specificity (or false positive rate). This binary classifier system (ROC curve) yielded a robust area under the curve AUC=0.984 (95% CI 0.932-1). AUC is a measure of how well a parameter can distinguish between two diagnostic groups, with 95% confidence interval (CI) from 0.93 to 1)

The data shown in the fore examples of the lactoferrin Elisa analysis were used to build a separate linear classifier model able to distinguish between AD pathological or non-pathological status. Receiver operating characteristic (ROC) analysis assesses the performance of the classifier models for group classification. A classifier model using the discovered lactoferrin levels from saliva analysis effectively classified Converters and healthy control groups with an area under the curve (AUC) of 0.98 with 95% (0.93-1) confidence interval (CI; FIG. 4A). This model yielded a sensitivity of 100% and specificity of 98.6%, for classifying the Converters and healthy control groups (FIG. 4A). This ROC curve, a fundamental tool for diagnostic test evaluation, evaluated the accuracy of the test to discriminate diseased cases from normal cases. The ROC can be understood as a plot of the probability of classifying correctly the positive samples against the rate of incorrectly classifying true negative samples. So the AUC measure of an ROC plot is a measure of predictive accuracy.

Figure 4B:
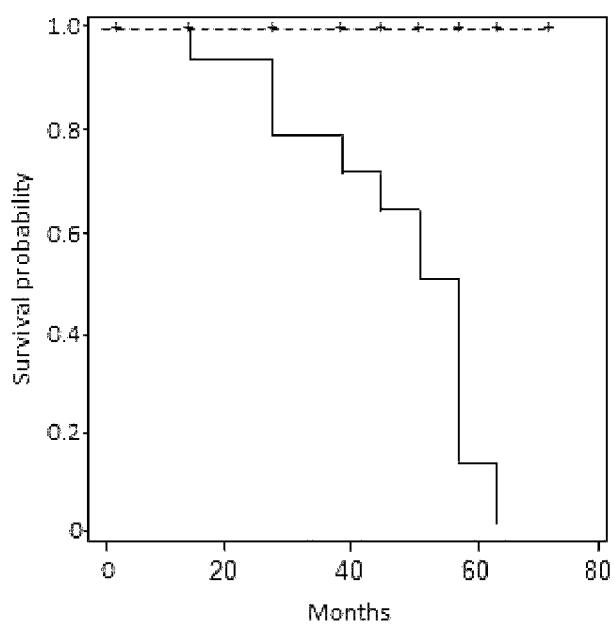
FIG. 4B shows the conversion to either aMCI or AD as predicted by salivary lactoferrin levels. The image shows the average time for phenoconversion to either aMCI or AD depending on abnormally reduced (Positives) or normal/high (Negatives) lactoferrin levels, based on the minimal Cox proportional hazards model. Dashed line is Negatives. Continuous line is Positives.

The probability to estimate the average time for phenoconversion to either aMCI or AD depending on abnormally reduced or normal/high lactoferrin levels was determined, using the Cox proportional hazards model (FIG. 4B). Our results show that salivary lactoferrin is an independent prognostic factor that predicts the probability of occurrence of AD, HR: 0.428 (95% CI 0.324-0.567; $p<0.0001$).

Figure 4C:
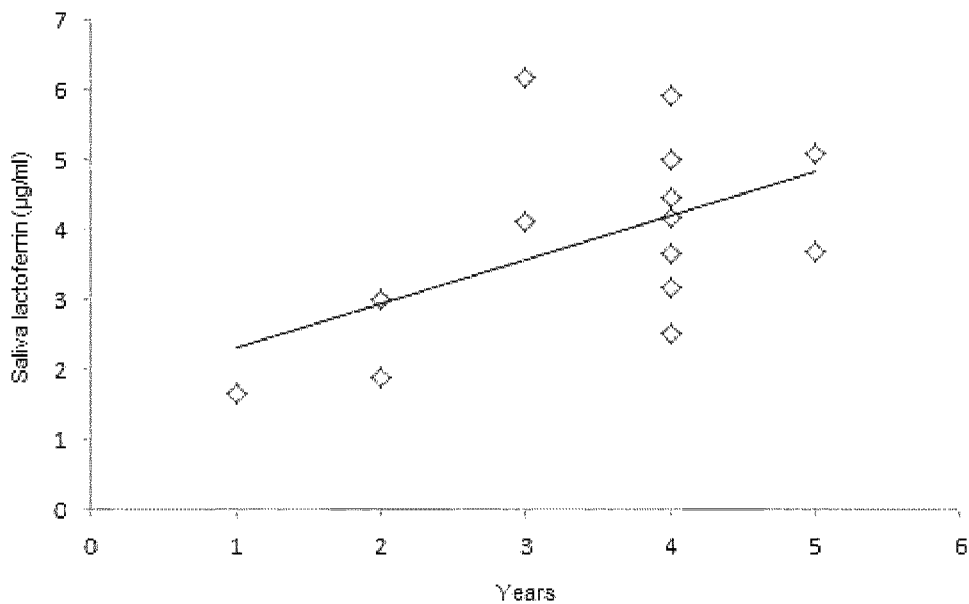
FIG. 4C shows a logistical regression analysis using lactoferrin expression values and time in years of onset or phenoconversion. The equation generated by regression analysis was y=0.6289x+1,6954.
Figure 5A:
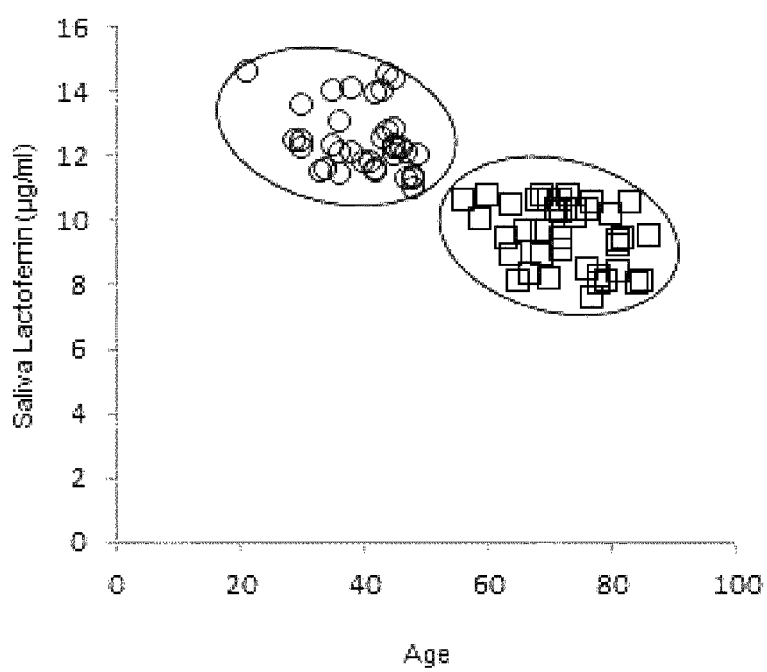
FIG. 5A shows a regression analysis using saliva lactoferrin values and age as accurate measurement to classify both young- and aged-healthy groups. ○ Young non-demented; □ Elderly non-demented.
Figure 5B:
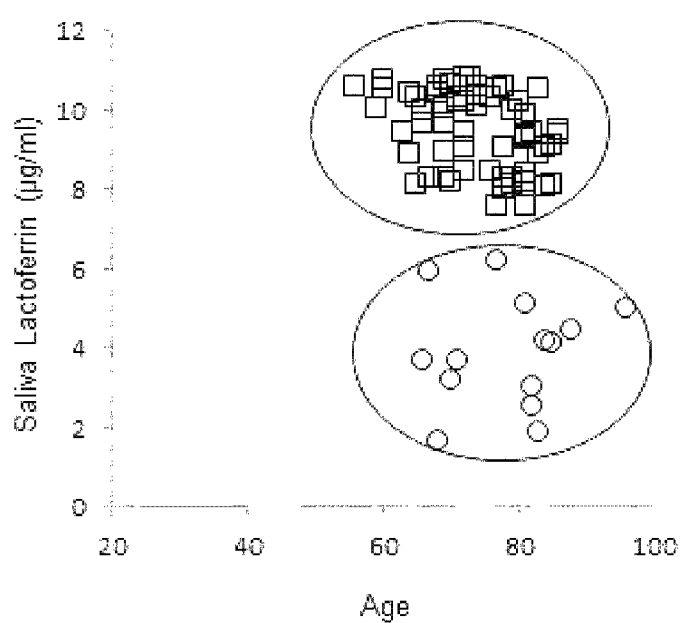
FIG. 5B shows a regression analysis using saliva lactoferrin expression values and age as accurate measurement to classify both aged-group (non-phenoconverters) and phenoconverters to MCI and AD. ○ Phenoconverters; □ Elderly non-demented.

In the present study, AUC=0.98 indicated a robust discrimination power, being 1 a perfect discrimination. Regression analysis generated an equation to describe this relationship between saliva lactoferrin levels and the time (years) of phenoconversion (onset), $y=0.6289x+1.6954$, being "y" the saliva lactoferrin levels, and "x" the time in years of phenoconversion (FIG. 4C).

The invention claimed is:

1. A method of detecting lactoferrin in a sample obtained from a subject having or at risk of having mild cognitive impairment (MCI) or Alzheimer's disease, the method comprising:
    detecting a level of lactoferrin protein in a saliva sample collected from the subject by contacting the sample with an antibody specific for lactoferrin and detecting specific binding of the antibody and lactoferrin, and determining whether the level of lactoferrin is above or below a value of 7.43 µg/ml.

2. The method of claim 1, wherein the subject is a mammal.

3. The method of claim 2, wherein the mammal is a human.

4. The method of claim 1, wherein the level of lactoferrin protein is detected using a lactoferrin human enzyme-linked immunosorbent assay (ELISA) kit.

5. The method of claim 1, wherein the sample comprises a protease inhibitor.

* * * * *

SEQUENCE LISTING

```
<160> NUMBER OF SEQ ID NOS: 1

<210> SEQ ID NO 1
<211> LENGTH: 711
<212> TYPE: PRT
<213> ORGANISM: Homo sapiens

<400> SEQUENCE: 1

Met Lys Leu Val Phe Leu Val Leu Leu Phe Leu Gly Ala Leu Gly Leu
1               5                   10                  15

Cys Leu Ala Gly Arg Arg Arg Arg Ser Val Gln Trp Cys Ala Val Ser
            20                  25                  30

Gln Pro Glu Ala Thr Lys Cys Phe Gln Trp Gln Arg Asn Met Arg Arg
```

-continued

```
            35                  40                  45
Val Arg Gly Pro Pro Val Ser Cys Ile Lys Arg Asp Ser Pro Ile Gln
 50                  55                  60

Cys Ile Gln Ala Ile Ala Glu Asn Arg Ala Asp Ala Val Thr Leu Asp
 65                  70                  75                  80

Gly Gly Phe Ile Tyr Glu Ala Gly Leu Ala Pro Tyr Lys Leu Arg Pro
                 85                  90                  95

Val Ala Ala Glu Val Tyr Gly Thr Glu Arg Gln Pro Arg Thr His Tyr
                100                 105                 110

Tyr Ala Val Ala Val Lys Lys Gly Gly Ser Phe Gln Leu Asn Glu
            115                 120                 125

Leu Gln Gly Leu Lys Ser Cys His Thr Gly Leu Arg Arg Asn Ala Gly
            130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
                180                 185                 190

Cys Ala Gly Thr Gly Glu Asn Lys Cys Ala Phe Ser Ser Gln Glu Pro
            195                 200                 205

Tyr Phe Ser Tyr Ser Gly Ala Phe Lys Cys Leu Arg Asp Gly Ala Gly
            210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
                260                 265                 270

His Ala Val Val Ala Arg Ser Val Asn Gly Lys Glu Asp Ala Ile Trp
            275                 280                 285

Asn Leu Leu Arg Gln Ala Gln Glu Lys Phe Gly Lys Asp Lys Ser Pro
            290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
                340                 345                 350

Lys Ser Glu Glu Glu Val Ala Ala Arg Arg Ala Arg Val Val Trp Cys
            355                 360                 365

Ala Val Gly Glu Gln Glu Leu Arg Lys Cys Asn Gln Trp Ser Gly Leu
            370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
                420                 425                 430

Glu Asn Tyr Lys Ser Gln Gln Ser Ser Asp Pro Asp Pro Asn Cys Val
            435                 440                 445

Asp Arg Pro Val Glu Gly Tyr Leu Ala Val Ala Val Val Arg Arg Ser
450                 455                 460
```

```
Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
            485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
            515                 520                 525

Gly Asp Glu Gln Gly Glu Asn Lys Cys Val Pro Asn Ser Asn Glu Arg
530                 535                 540

Tyr Tyr Gly Tyr Thr Gly Ala Phe Arg Cys Leu Ala Glu Asp Ala Gly
545                 550                 555                 560

Asp Val Ala Phe Val Lys Gly Val Thr Val Leu Gln Asn Thr Asp Gly
            565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
            675                 680                 685

Ala Gly Ile Thr Asn Leu Lys Lys Cys Ser Thr Ser Pro Leu Leu Glu
            690                 695                 700

Ala Cys Glu Phe Leu Arg Lys
705                 710
```